(12) United States Patent
Min et al.

(10) Patent No.: US 10,209,172 B2
(45) Date of Patent: Feb. 19, 2019

(54) VISCOSITY MEASUREMENT DEVICE

(71) Applicant: LG CHEM, LTD., Seoul (KR)

(72) Inventors: Kyounghoon Min, Daejeon (KR);
Sunghyun Park, Daejeon (KR);
Yehoon Im, Daejeon (KR)

(73) Assignee: LG Chem, Ltd., Seoul (KR)

( * ) Notice: Subject to any disclaimer, the term of this patent is extended or adjusted under 35 U.S.C. 154(b) by 125 days.

(21) Appl. No.: 15/531,286

(22) PCT Filed: Dec. 18, 2015

(86) PCT No.: PCT/KR2015/013923
§ 371 (c)(1),
(2) Date: May 26, 2017

(87) PCT Pub. No.: WO2016/099190
PCT Pub. Date: Jun. 23, 2016

(65) Prior Publication Data
US 2017/0363452 A1   Dec. 21, 2017

(30) Foreign Application Priority Data

Dec. 18, 2014   (KR) .......................... 10-2014-0183223

(51) Int. Cl.
*G01N 11/12* (2006.01)
*G01F 1/00* (2006.01)
(Continued)

(52) U.S. Cl.
CPC .............. *G01N 11/12* (2013.01); *G01F 1/00* (2013.01); *G01N 11/02* (2013.01); *G01N 11/04* (2013.01);
(Continued)

(58) Field of Classification Search
CPC ........ G01N 11/00; G01N 11/02; G01N 11/10; G01N 11/105; G01N 11/12; G01N 2011/0086
See application file for complete search history.

(56) References Cited

U.S. PATENT DOCUMENTS

| 3,282,323 A | 11/1966 | Katz et al. |
| 3,717,026 A * | 2/1973 | Ito ........................... G01N 11/12 73/54.21 |

(Continued)

FOREIGN PATENT DOCUMENTS

| EP | 0 014 164 B1 | 8/1980 |
| GB | 1493527 A | 11/1977 |

(Continued)

*Primary Examiner* — Justin N Olamit
(74) *Attorney, Agent, or Firm* — Dentons US LLP

(57) ABSTRACT

The present invention relates to a viscosity measurement device. According to one aspect of the present invention, provided is a viscosity measurement device comprising: a housing which has an inlet port, an outlet port and a measurement space positioned between the inlet port and the outlet port; a magnetic body arranged in the measurement space; an electromagnet for moving the magnetic body; a position measurement part for measuring the position of the magnetic body; a flow rate measurement part for measuring the flow rate of fluid which flows in the measurement space; and a control part for measuring the viscosity of the fluid on the basis of the strength of a magnetic field generated by the electromagnet and the shear strain rate of the fluid which passes through the measurement space.

18 Claims, 2 Drawing Sheets

(51) Int. Cl.
*G01N 11/10* (2006.01)
*G01N 11/02* (2006.01)
*G01N 11/04* (2006.01)
*G01N 11/00* (2006.01)

(52) U.S. Cl.
CPC ...... *G01N 11/10* (2013.01); *G01N 2011/0086* (2013.01)

(56) References Cited

U.S. PATENT DOCUMENTS

| | | | |
|---|---|---|---|
| 4,003,255 A * | 1/1977 | Spencer | G01F 1/20 137/486 |
| 4,627,272 A | 12/1986 | Wright | |
| 5,277,058 A | 1/1994 | Kalyon et al. | |

FOREIGN PATENT DOCUMENTS

| | | |
|---|---|---|
| IL | 58958 A | 12/1982 |
| JP | 61-239118 A | 10/1986 |
| WO | 2014/035428 A1 | 3/2014 |

\* cited by examiner

[Figure 1]
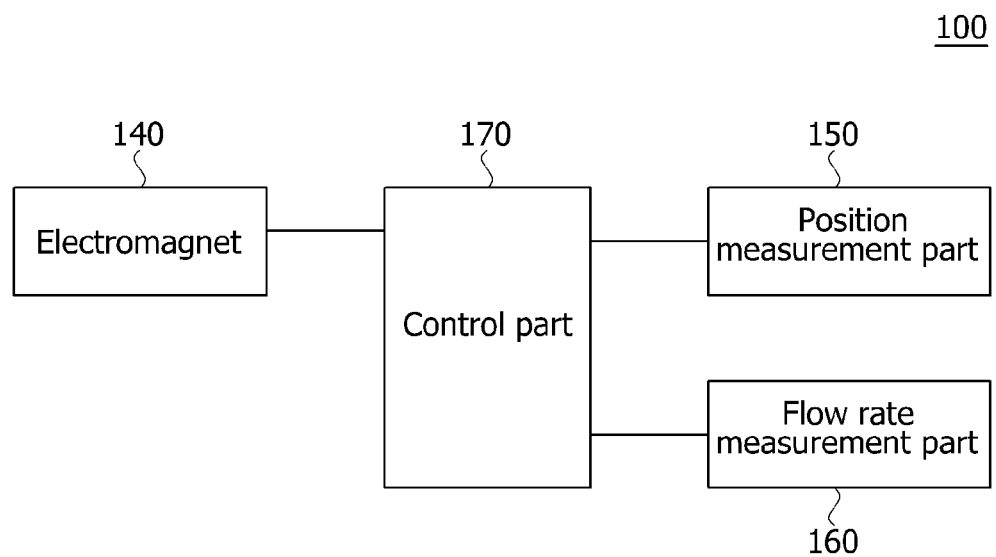
[Figure 2]
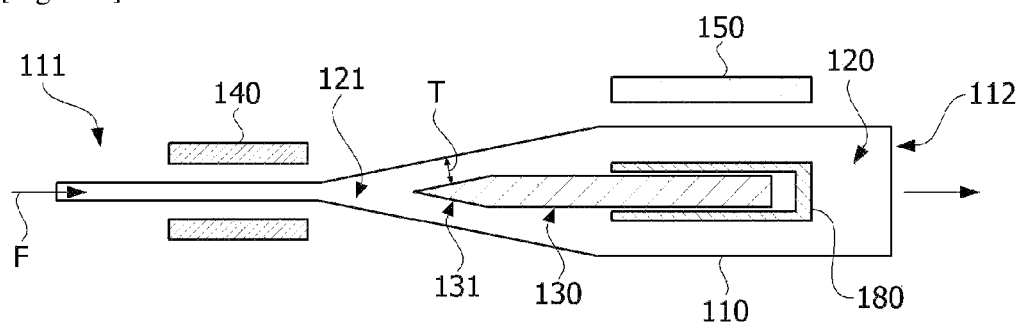
[Figure 3]
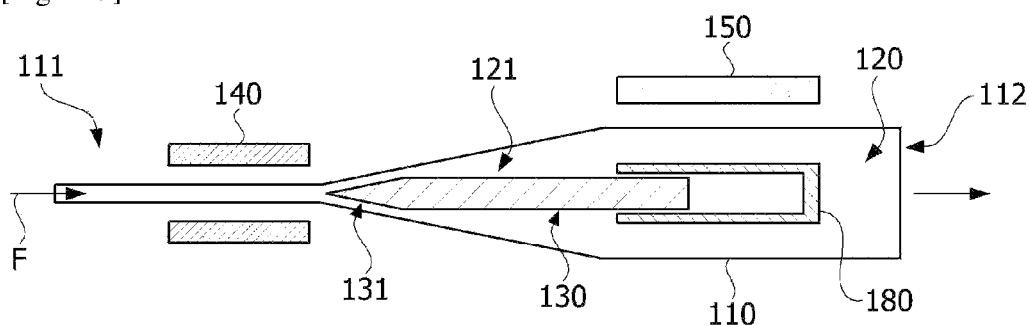

[Figure 4]
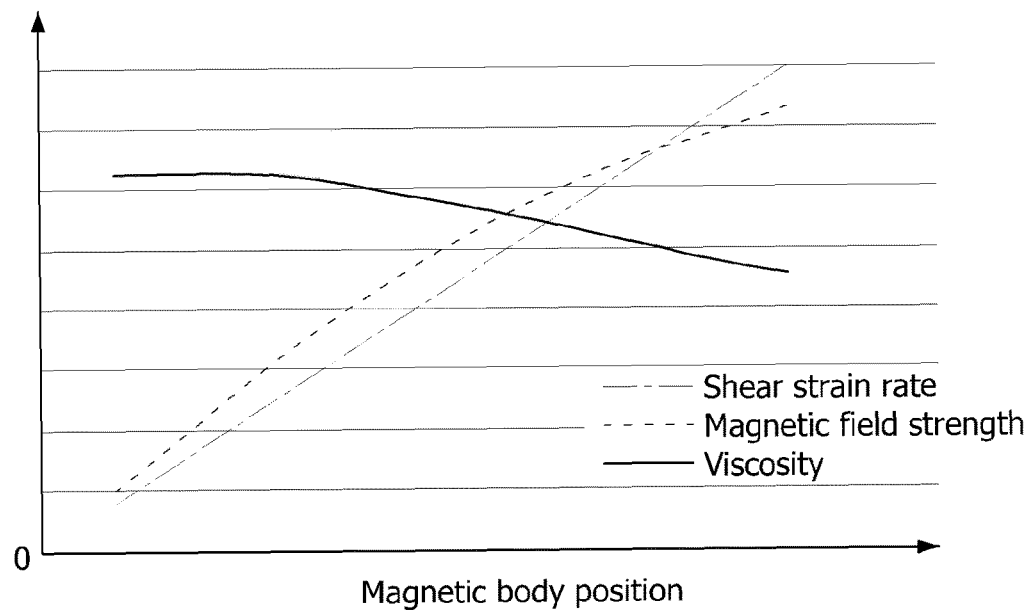

VISCOSITY MEASUREMENT DEVICE

This application is a National Stage Application of International Application No. PCT/KR2015/013923 filed on Dec. 18, 2015, which claims the benefit of Korean Patent Application No. 10-2014-0183223 filed on Dec. 18, 2014, all of which are hereby incorporated by reference in their entirety for all purposes as if fully set forth herein.

TECHNICAL FIELD

The present invention relates to a viscosity measurement device, and more particularly, to a viscosity measurement device capable of measuring a viscosity of a fluid according to shear strain rates.

The present invention claims the benefit of priority based on Korea Patent Application No. 10-2014-0183223 filed on Dec. 18, 2014, the disclosure of which is incorporated by reference in its entirety.

BACKGROUND ART

Generally, in processes of preparing materials in a liquid state such as polymer preparing processes, viscosities of intermediate products and viscosities of reactants in a reactor are important information for managing reaction conversion rates and product qualities.

Furthermore, viscosities of polymer solutions or suspensions, and the like vary depending on shear strain rates acting on fluids. However, since the conventionally used online viscometers can measure only viscosities of specific shear strain rates, they have a limit difficult to accurately measure rheological characteristics of fluids.

DISCLOSURE

Technical Problem

It is a problem to be solved in the present invention to provide a viscosity measurement device capable of measuring a viscosity of a fluid according to shear strain rates.

Technical Solution

In order to solve the above problems, according to one aspect of the present invention, a viscosity measurement device is provided, which comprises a housing having an inlet port, an outlet port and a measurement space positioned between the inlet port and the outlet port, respectively; a magnetic body arranged in the measurement space; an electromagnet for moving the magnetic body; a position measurement part for measuring a position of the magnetic body; a flow rate measurement part for measuring a flow rate of a fluid which flows in the measurement space; and a control part for measuring a viscosity of the fluid on the basis of strength of a magnetic field generated by the electromagnet and a shear strain rate of the fluid which passes through the measurement space.

Also, according to another aspect of the present invention, a viscosity measurement device is provided, which comprises a housing having an inlet port, an outlet port and a measurement space positioned between the inlet port and the outlet port, respectively; a magnetic body arranged in the measurement space; an electromagnet for slidingly moving the magnetic body toward the inlet port side; a position measurement part for measuring a position of the magnetic body; a flow rate measurement part for measuring a flow rate of a fluid which flows in the measurement space; and a control part for calculating a viscosity of the fluid on the basis of a shear strain rate of the fluid which passes through the measurement space at the position of the relevant magnetic body, where the position of the magnetic body in the measurement space varies as strength of a magnetic field generated by the electromagnet changes.

Furthermore, according to another aspect of the present invention, a viscosity measurement device installed in a pipeline through which a fluid flows in a reactor or a facility is provide, which comprises a housing, having a measurement space, for being mounted to the pipeline; a magnetic body disposed in the measurement space; an electromagnet for slidingly moving the magnetic body in a direction opposite to a flow direction of the fluid; a position measurement part for measuring a position of the magnetic body; a flow rate measurement part for measuring a flow rate of the fluid passing through the pipeline; and a control part for generating a magnetic field by supplying a current to the electromagnet to move the magnetic body, measuring a shear strain rate of the fluid on the basis of the flow rate of the fluid and the position of the moved magnetic body and measuring a viscosity of the fluid on the basis of strength of the magnetic field and the shear strain rate.

Advantageous Effects

As described above, the viscosity measurement device related to one embodiment of the present invention has the following effects.

The position of the magnetic body can be changed by changing the strength of the magnetic field. In addition, the viscosity of the fluid according to shear strain rates can be measured at the position of the magnetic body. Accordingly, the viscosity of each fluid can be measured according to various shear strain rates, as the strength of the magnetic field is changed to measure the position of the magnetic body.

BRIEF DESCRIPTION OF DRAWINGS

FIG. 1 is a configuration diagram of the viscosity measurement device related to one embodiment of the present invention.

FIGS. 2 and 3 are conceptual diagrams for explaining one operating state of the viscosity measurement device related to one embodiment of the present invention.

FIG. 4 is a graph showing viscosities according to the strength of the magnetic field and the shear strain rates.

MODE FOR INVENTION

Hereinafter, the viscosity measurement device according to one embodiment of the present invention will be described in detail with reference to the accompanying drawings.

In addition, the same or similar reference numerals are given to the same or corresponding components regardless of the reference numerals, where their duplicate explanations will be omitted, and for convenience of explanation, the size and shape of each constituent member shown may be exaggerated or reduced.

FIG. 1 is a configuration diagram of the viscosity measurement device (100) related to one embodiment of the present invention, FIGS. 2 and 3 are conceptual diagrams for explaining one operating state of the viscosity measurement device related to one embodiment of the present invention, and FIG. 4 is a graph showing viscosities according to the strength of the magnetic field and the shear strain rates.

The viscosity measurement device (100) related to one embodiment of the present invention comprises a housing (110) and a magnetic body (130) and an electromagnet (140) and a position measurement part (150) and a flow rate measurement part (160), and a control part (170).

The housing (110) has an inlet port (111) and an outlet port (112). In addition, the housing (110) comprises a measurement space (120) positioned between the inlet port (111) and the outlet port (112). Also, a flow direction of a fluid (F) passing through the housing (110) is a direction facing the outlet port (112) from the inlet port (111).

Furthermore, the viscosity measurement device (100) may be a viscosity measurement device installed in a pipeline through which a fluid flows in a reactor or a facility, and for example, nay be an in-line viscosity measurement device. Here, the housing (110) is mounted on the pipeline, and the fluid flowing along the pipeline passes through the inlet port (111) and the measurement space (120) and the outlet port (112) in order.

The magnetic body (130) is disposed in the measurement space (120). The magnetic body (130) can be formed of a material capable of moving by a magnetic force if the magnetic field is applied. In addition, the magnetic body (130) may have various shapes, if necessary. For example, the magnetic body (130) may be provided to have a columnar shape (cylindrical, polygonal column, etc.), a spherical shape or the like.

In addition, the electromagnet (140) is provided so as to move the magnetic body (130) by generating a magnetic field when power is supplied. In one embodiment, the electromagnet (140) may be provided with a coil. The electromagnet (140) is provided to move the magnetic body (130) toward the inlet port (111) side by generating a magnetic field. Also, the electromagnet (140) is provided to slidingly move the magnetic body (130) toward the inlet port (111) side by generating a magnetic field. Also, the electromagnet (140) is provided to slidingly move the magnetic body (130) in a direction opposite to a flow direction of the fluid (F). Also, when the fluid (F) is introduced into the measurement space, the magnetic body (130) is moved in a direction opposite the flow direction of the fluid (F) by a magnetic field generated from the electromagnet (140).

In addition, the position measurement part (150) performs a function for measuring a position of the magnetic body (130). The position measurement part (150) may be configured using a conventional camera or laser. The position change amount of the magnetic body (130) can be measured and calculated by measuring the initial position and the moved position of the magnetic body (130), respectively, through the position measurement part (150). Also, the flow rate measurement part (160) performs a function for measuring a flow rate of the fluid (F) flowing in the measurement space (120). Furthermore, the flow rate measurement part (160) may be provided to measure the flow rate of the fluid passing through the above-described pipeline.

The control part (170) is provided to measure the viscosity of the fluid (F) on the basis of strength of the magnetic field generated by the electromagnet (140) and shear strain rates of the fluid (F) passing through the measurement space (120).

The shear strain rate is a velocity change rate of the fluid according to the position, which may be represented by Equation 1 below, if in general, a velocity of a fluid is denoted by v and a distance from the reference point is denoted by x. In Equation 1 below, the left-hand column on the basis of=represents the shear strain rate.

$$\dot{\gamma} = \frac{\partial v}{\partial x} \quad \text{[Equation 1]}$$

In the present invention, the shear strain rate is proportional to the flow rate of the fluid and inversely proportional to the distance between the magnetic body and the housing. The velocity v can be calculated by dividing the flow rate Q of the fluid by the flow passage area A between the magnetic body and the housing, and if an interval between the magnetic body and the housing is denoted by T, the shear strain rate may be represented by Equation 2 below. In Equation 2 below, the left-hand column on the basis of=represents the shear strain rate.

$$\dot{\gamma} = a\frac{Q/A}{T} \quad \text{[Equation 2]}$$

In Equation 2 above, α is a proportional constant in accordance with the shape and size of the magnetic body and the housing.

The interval between the magnetic body and the housing can be changed by the strength of the magnetic field applied to the magnetic body, and when the strength of the magnetic field applied to the magnetic body is the same, the interval between the magnetic body and the housing can be changed depending on the viscosity of the fluid.

The viscosity (η) of the fluid is a ratio of a shear stress (τ) applied to the fluid and the shear strain rate, which may be represented by Equation 3 below.

$$\eta = \frac{\tau}{\dot{\gamma}} \quad \text{[Equation 3]}$$

When the shear strain rate is constant, that is, the flow rate, and the interval between the magnetic body and the housing are constant, the shear stress applied to the fluid is proportional to the strength of the magnetic field applied to the magnetic body. Thus, the strength of the magnetic field may be determined based on the product of the viscosity and the shear strain rate, whereby the viscosity of the fluid (F) can be measured (calculated) on the basis of the strength of the magnetic field and the shear strain rate.

Moreover, the electromagnet (140) may be provided to move the magnetic body (130) from the measurement space (120) toward the inlet port (111) side. In addition, the electromagnet (140) may be provided to translationally move the magnetic body (130). For this purpose, the viscosity measurement device (100) may comprise a guide member (180) provided in the measurement space (120) in order to guide the translational movement of the magnetic body (130). Specifically, the guide member (180) may be provided to surround at least some region of the magnetic body (130) in order to guide the sliding movement of the magnetic body (130). In addition, the guide member (180) may be also provided to be opened toward the inlet port (111) side of the housing (110) and to be closed toward the outlet port (112) side of the housing (110). Furthermore, the guide member (180) may be also closed toward the outlet port (112) side of the housing (110) and also have a structure that does not pass the magnetic body, while passing the fluid.

In addition, the magnetic body (130) slidingly moves from the measurement space (120) toward the inlet port (111) side, if the magnetic field is generated by the guide member (180) and the electromagnet (140). Furthermore, the guide member (180) may be provided to guide and support the sliding movement of the magnetic body (130) in contact with at least some region of the magnetic body (130).

Besides, the control part (170) may determine the shear strain rate on the basis of the position of the magnetic body (130) and the flow rate of the fluid flowing in the measurement space (120). For example, referring to FIG. 2, the shear strain rate may be proportional to the flow rate of the fluid (F) and inversely proportional to the interval (T) of the magnetic body (130) and the measurement space (120). Here, the interval (T) of the magnetic body (130) and the measurement space (120) can be measured via the position measurement part (150). FIG. 2 represents the position of the magnetic body (130) at a relatively low shear strain rate, and FIG. 3 represents the position of the magnetic body (130) at a relatively high shear strain rate. Specifically, when the magnetic body (130) is moved by applying the same magnetic field, the shear strain rate of the fluid (F) is reduced, if the interval (T) is large. Furthermore, if the interval (T) is small, the shear strain rate of the fluid (F) is increased. In short, in a state where the same magnetic field is applied, the higher the shear strain of the fluid (F), the magnetic body (130) can move further toward the inlet port (111) side.

In addition, the control part (170) may measure the viscosity based on the position of the magnetic body (130) where the magnetic force acting on the magnetic body (130) and the shear stress of the fluid (F) are balanced. FIGS. 2 and 3 show a state that the magnetic force acting on the magnetic body (130) and the shear stress of the fluid (F) are balanced, respectively. More specifically, when the strength of the magnetic field generated by the electromagnet (140) varies, the position of the magnetic body (130) in the measurement space (120) varies. Here, the control part (170) calculates the viscosity of the fluid (F) on the basis of the shear strain rate of the fluid (F) passing through the measurement space (120) at the position of the relevant magnetic body (130). In addition, the position of the magnetic body (130) for measuring the viscosity is a position where the magnetic force by the magnetic field and the shear stress required for the fluid (F) to pass between the magnetic body (130) and the measurement space (120) are balanced.

In addition, the control part (170) generates a magnetic field by supplying a current to the electromagnet (140) so as to move the magnetic body (130), measures the shear strain rate of the fluid (F) based on the flow rate of the fluid (F) and the position (or the above-described interval) of the moved magnetic body (130) and measures (calculates) the viscosity of the fluid based on the strength of the magnetic field and the shear strain rate.

Besides, the measurement space (120) may comprise a expansion region (121), the diameter of which increases further away from the inlet port (111), on the inlet port (111) side. For example, referring to FIGS. 2 and 3, the expansion region (121) may be provided so as to have a truncated conical shape.

In addition, the magnetic body (130) may be provided with an inclined end portion (131) whose diameter becomes smaller, as the end portion facing the inlet port (111) is closer to the inlet port (111) side. Here, the inclined surface of the expansion region (121) and the inclined surface of the inclined end portion (131) may be provided to have the same slope. Furthermore, the shear strain rate is measured on the basis of the interval (T) between the inclined surface of the inclined end portion (131) and the inclined surface of the expansion region (121). Also, the interval (T) is a value corresponding to the position variation amount of the magnetic body (130).

As described above, the position of the magnetic body can be changed according to changing the strength of the magnetic field.

Referring to FIG. 4, the viscosity of the fluid according to the shear strain rates of the fluid may be measured at the position of the magnetic body (130). Therefore, as the position of the magnetic body (130) is measured by changing the strength of the magnetic field, the viscosity of each fluid (F) according to various shear strain rates may be measured. The horizontal axis of FIG. 4 represents the position of the magnetic body, where 0 represents the initial position of the magnetic field, that is, a state close to the guide member side as a state where no magnetic field is applied to the magnetic body. Also, a state is shown, in which the magnetic body moves to the inlet port side of the housing toward the right side of the horizontal axis.

Preferred embodiments of the present invention described above have been disclosed for illustrative purposes, and it will be possible for those skilled in the art having the ordinary knowledge of the present invention to perform various modifications, alterations and additions thereof within the spirit and scope of the present invention, where these modifications, alterations, and additions will be regarded as falling within the following claims.

The invention claimed is:

1. A viscosity measurement device comprising:
   a housing having an inlet port and an outlet port and a measurement space positioned between the inlet port and the outlet port, respectively;
   a magnetic body arranged in the measurement space;
   an electromagnet for moving the magnetic body;
   a position measurement part for measuring a position of the magnetic body;
   a flow rate detector for measuring a flow rate of a fluid which flows in the measurement space; and
   a controller for measuring a viscosity of the fluid on the basis of strength of a magnetic field generated by the electromagnet and a shear strain rate of the fluid which passes through the measurement space.

2. The viscosity measurement device according to claim 1, wherein
   the electromagnet is provided so as to move the magnetic body from the measurement space toward an inlet port side.

3. The viscosity measurement device according to claim 2, wherein
   the electromagnet is provided so as to translationally move the magnetic body.

4. The viscosity measurement device according to claim 3, further comprising
   a guide member provided in the measurement space in order to guide the translational movement of the magnetic body.

5. The viscosity measurement device according to claim 4, wherein
   the guide member is provided to be opened toward the inlet port side of the housing and to be closed toward an outlet port side.

6. The viscosity measurement device according to claim 1, wherein
the controller determines the shear strain rate on the basis of the position of the magnetic body and the flow rate of the fluid flowing in the measurement space.

7. The viscosity measurement device according to claim 6, wherein
the controller measures the viscosity based on the position of the magnetic body where a magnetic force acting on the magnetic body and a shear stress of the fluid are balanced.

8. The viscosity measurement device according to claim 6, wherein
the measurement space comprises an expansion region, a diameter of which increases further away from the inlet port, on an inlet port side.

9. The viscosity measurement device according to claim 8, wherein
the expansion region is provided so as to have a truncated conical shape.

10. The viscosity measurement device according to claim 8, wherein
the magnetic body is provided with an inclined end portion whose diameter becomes smaller, as the end portion facing the inlet port is closer to the inlet port side.

11. The viscosity measurement device according to claim 10, wherein
the shear strain rate is measured on the basis of an interval between an inclined surface of the inclined end portion and an inclined surface of the expansion region.

12. A viscosity measurement device comprising:
a housing having an inlet port and an outlet port and a measurement space positioned between the inlet port and the outlet port, respectively;
a magnetic body arranged in the measurement space;
an electromagnet for slidingly moving the magnetic body toward an inlet port side;
a position measurement part for measuring a position of the magnetic body;
a flow rate detector for measuring a flow rate of a fluid which flows in the measurement space; and
a controller for calculating a viscosity of the fluid on the basis of a shear strain rate of the fluid which passes through the measurement space at the position of the magnetic body, where the position of the magnetic body in the measurement space varies as strength of a magnetic field generated by the electromagnet changes.

13. The viscosity measurement device according to claim 12, wherein
the position of the magnetic body for measuring the viscosity is a position where a magnetic force by the magnetic field and a shear stress required for the fluid to pass between the magnetic body and the measurement space are balanced.

14. The viscosity measurement device according to claim 12, further comprising
a guide member provided to surround at least some region of the magnetic body in order to guide the sliding movement of the magnetic body.

15. The viscosity measurement device according to claim 12, wherein
the measurement space comprises an expansion region, a diameter of which increases further away from the inlet port, on the inlet port side,
the magnetic body is provided with an inclined end portion whose diameter becomes smaller, as an end portion facing the inlet port is closer to the inlet port side, and
an inclined surface of the expansion region and an inclined surface of the inclined end portion are provided to have the same slope.

16. The viscosity measurement according to claim 15, wherein
the shear strain rate is measured on the basis of an interval between the inclined surface of the inclined end portion and the inclined surface of the expansion region.

17. A viscosity measurement device installed in a pipeline through which a fluid flows in a reactor or a facility, comprising:
a housing, having a measurement space, for being mounted to the pipeline;
a magnetic body disposed in the measurement space;
an electromagnet for slidingly moving the magnetic body in a direction opposite to a flow direction of the fluid;
a position measurement part for measuring a position of the magnetic body;
a flow rate detector for measuring a flow rate of the fluid passing through the pipeline; and
a controller for generating a magnetic field by supplying a current to the electromagnet to move the magnetic body, measuring a shear strain rate of the fluid on the basis of the flow rate of the fluid and the position of the moved magnetic body and measuring a viscosity of the fluid on the basis of strength of the magnetic field and the shear strain rate.

18. The viscosity measurement device according to claim 17, further comprising
a guide member provided to surround at least some region of the magnetic body in order to guide the sliding movement of the magnetic body.

* * * * *